(12) United States Patent
Agarwal et al.

(10) Patent No.: US 11,793,741 B2
(45) Date of Patent: Oct. 24, 2023

(54) TOPICAL COMPOSITION

(71) Applicant: Conopco, Inc., Trumbull, CT (US)

(72) Inventors: Khushbu Agarwal, Bangalore (IN);
Balu Kunjupillai, Bangalore (IN);
Amitabha Majumdar, Bangalore (IN)

(73) Assignee: CONOPCO, INC., Englewood Cliffs, NJ (US)

( * ) Notice: Subject to any disclaimer, the term of this patent is extended or adjusted under 35 U.S.C. 154(b) by 306 days.

(21) Appl. No.: 16/766,830

(22) PCT Filed: Dec. 17, 2018

(86) PCT No.: PCT/EP2018/085239
§ 371 (c)(1),
(2) Date: May 26, 2020

(87) PCT Pub. No.: WO2019/121529
PCT Pub. Date: Jun. 27, 2019

(65) Prior Publication Data
US 2020/0315939 A1 Oct. 8, 2020

(30) Foreign Application Priority Data
Dec. 18, 2017 (IN) .................. 17208124.2

(51) Int. Cl.
*A61K 8/49* (2006.01)
*A61K 8/67* (2006.01)
*A61Q 15/00* (2006.01)
*A61Q 17/00* (2006.01)

(52) U.S. Cl.
CPC ............ *A61K 8/4926* (2013.01); *A61K 8/675* (2013.01); *A61Q 15/00* (2013.01); *A61Q 17/005* (2013.01)

(58) Field of Classification Search
CPC .................................................. A61K 8/4926
See application file for complete search history.

(56) References Cited

U.S. PATENT DOCUMENTS

| | | | |
|---|---|---|---|
| 3,464,998 A | 9/1969 | Krimmel et al. | |
| 3,822,277 A * | 7/1974 | Dufour ............... | C07D 213/81 546/323 |
| 3,983,126 A | 9/1976 | Dufour | |
| 8,252,818 B2 | 8/2012 | Aston et al. | |
| 2001/0049382 A1 | 12/2001 | Jacobson et al. | |
| 2011/0123510 A1 | 5/2011 | Imai et al. | |
| 2013/0052162 A1 | 2/2013 | Koeffler et al. | |
| 2014/0031310 A1 | 1/2014 | Maki et al. | |
| 2014/0329674 A1 | 11/2014 | Woods et al. | |
| 2016/0176806 A1 | 6/2016 | Mondiere et al. | |
| 2020/0315939 A1 | 10/2020 | Agarwal et al. | |
| 2022/0087914 A1 | 3/2022 | Kapoor et al. | |

FOREIGN PATENT DOCUMENTS

| | | | |
|---|---|---|---|
| CA | 2918832 | 2/2015 | |
| CN | 101715786 | 6/2010 | |
| CN | 105028416 | 11/2015 | |
| CN | 105123698 | 12/2015 | |
| EP | 2742942 | 6/2014 | |
| EP | 3120850 | 1/2017 | |
| ES | 2329642 | 11/2009 | |
| FR | 1568105 | 5/1969 | |
| GB | 1235348 | 12/1968 | |
| GB | 1244320 | 12/1968 | |
| WO | WO-2011133692 A1 * | 10/2011 | ........... A61K 31/455 |
| WO | WO2015172801 | 11/2015 | |
| WO | WO2015196036 | 12/2015 | |
| WO | WO2016073633 | 5/2016 | |
| WO | WO2017060213 | 4/2017 | |

OTHER PUBLICATIONS

Computer Software; ChemDraw Professional; 2022; Version 20.1; PerkinElmer Informatics.
Search Report and Written Opinion in PCTEP2018085239; dated Feb. 20, 2019.
Search Report and Written Opinion in EP17208124; dated Jun. 6, 2018.
Database Registry (Online); Chemical Abstracts Service, Columbus, OH, US; Apr. 30, 2001, XP002781274; Database accession No. 333430-06-1.
Database Registry (Online); Chemical Abstracts Service, Columbus, OH, US; Feb. 11, 2016, XP002781273, Database accession No. 1864685-46-1.
Search Report and Written Opinion in EP17208131; dated Jun. 11, 2018.
Do et al.; Photoinduced, Copper-Catalyzed Alkylation of Amides with Unactivated Secondary Alkyl Halides at Room Temperature; Journal of the American Chemical Society; 2014; pp. 2162-2167; XP55477549; vol. 136, No. 5.

(Continued)

*Primary Examiner* — Gina C Justice
(74) *Attorney, Agent, or Firm* — Krista A. Kostiew

(57) ABSTRACT

The present invention relates to a topical composition comprising from 0.001 to 10% by weight a compound of formula (I), i.e. N-cyclopropyl nicotinamide, that provides improved antimicrobial effect through generation of antimicrobial peptides when applied to an external surface of the human body. A combination of compound of formula I and at least one ingredient selected from niacinamide, picolinamide and iso-nicotinamide triggers generation of AMPs in a synergistic way.

(I)

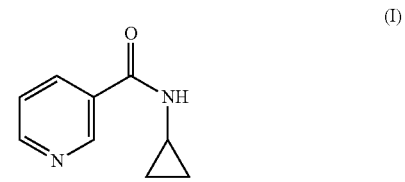

16 Claims, No Drawings

(56) References Cited

OTHER PUBLICATIONS

Cote et al.; Studies On Nicotinamide Derivatives; Journal of Bacteriology; 1951; pp. 463-467; XP002560848; vol. 61, No. 4.
Sikder et al.; Quaternary Salts of 3,3'-Bis-Pyridinium Monooximes: Synthesis and Biological Activity Journal of Pharmaceutical Sciences; 1993; pp. 258-261; XP000909817; vol. 82, No. 3.
IPRP2 in PCTEP2018085269; dated Dec. 6, 2019.
Search Report and Written Opinion in PCTEP2018085269; dated Mar. 14, 2019.
Co-pending Application, Agarwal et al., May 2020, U.S. Appl. No. 16/766,834.
M.H. Braff and R.L. Gallo; Antimicrobial Peptides; An Essential Component of the Skin Defensive Barrier; 2006; pp. 1-20; vol. 306:91-100; Springer-Verlag Berlin Heidelberg.
IPRP1 in PCTEP2018085239; dated Jun. 23, 2020; World Intellectual Property Org. (WIPO).
Aurora Fine Chemicals Chemcats; 3-Pyridinecarboxamide, N-cyclopentyl-, hydrochloride; CAS STN registry Database (online) Chemical Library; Jun. 25, 2015; pp. 1, Reigstry No. 1788767-86-1.
CA, CAPLUS, CASFORMULTNS, CHEMCATS, USPATFULL; 3-Pyridinecarboxamide, N-cyclopentyl-; CAS STN Registry Database (online); Apr. 30, 2001; pp. 1, Registry No. 333430-06-1.

\* cited by examiner

TOPICAL COMPOSITION

CROSS REFERENCE TO RELATED APPLICATIONS

The present application is a U.S. National Phase Application under 35 U.S.C. § 371 of International Application No. PCT/EP2018/085239, filed on Dec. 17, 2018, which claims priority to European Patent Application No. 17208124.2, filed on Dec. 18, 2017, the contents of which are incorporated herein in their entireties.

FIELD OF THE INVENTION

The present invention relates to a topical composition and more particularly to a topical composition for providing an antimicrobial benefit.

BACKGROUND OF THE INVENTION

People generally try to take good care of themselves to enjoy a healthy lifestyle. Often, this includes taking care of their external surfaces like e.g. skin, scalp, hair and oral cavity. One of the ways people try to take care of their external surfaces is by using topical compositions that deliver various benefits like dandruff-free scalp, thick and strong hair, oral cavity that is free of caries, malodour and antimicrobial benefits, i.e. keeping external surfaces free of microorganisms such as bacteria and some fungi.

Many if not all the problems people face, are associated with getting exposed to microorganisms like e.g. bacteria and some fungi. For example, dandruff is associated with fungal microorganisms and dental caries and malodour too; are generally associated with presence of bacteria in the oral cavity. In addition, there are bacteria like *Escherichia coli* (*E. coli*) and *Staphylococcus aureus* (*S. aureus*) that are commonly found on the surfaces of the human skin like e.g. on hands. While these bacteria are not pathogenic whilst being present on the skin, they may become pathogenic if they enter the human body through ingestion.

Therefore, people generally want to get rid of or at least minimize getting exposed to microorganisms that are harmful or may become harmful. One way people try to obtain this is through application of an antimicrobial compound after an infection has set in. Whereas, another way is to leave on the external surfaces like e.g. on the skin, a minimal amount of a compound that induces generation of antimicrobial peptides (AMPs) like e.g. psoriasin from the skin.

AMPs form an integral part of the skin's own defense system. AMPs were initially discovered in insects and in animals and ever since their initial discovery, AMPs are regarded as promising antimicrobials. AMPs are ubiquitous in nature and they typically exhibit a broad spectrum of activity against invading bacteria, fungi, enveloped viruses and parasites (Braff and Gallo, 2006). AMPs are generally short peptides and in humans about 90 different AMPs are reported to be present.

A few references are found in prior art that describe compounds like niacinamide for generation of AMPs.

WO 2015/172801 (Unilever, 2015) discloses a new use of niacinamide for triggering generation of AMPs on skin. This has application in improving the immunity of skin, scalp and oral cavity against attack by microorganisms.

Further, FR1568105 (M. Claude Dufour) discloses the preparation process for preparing a compound N-cyclopropyl nicotinamide.

Despite there exists technologies, people are often on a look-out for newer technologies that will deliver improved antimicrobial benefit through generation of AMPs thereby improving the immunity of skin, scalp and oral cavity.

Need therefore exists to provide topical compositions comprising one or more compounds that provide an improved antimicrobial benefit through improved generation of AMPs.

It is therefore an objective of the present invention to provide a topical composition that provides improved antimicrobial benefit through improved generation of AMPs.

The present inventors have surprisingly found that a compound of formula I, i.e. N-cyclopropyl nicotinamide, when applied to the human skin, induces generation of AMPs. Further, it has also been surprisingly found that the compound of formula I and at least one compound selected from niacinamide, picolinamide and iso-nicotinamide when used in combination at select concentrations, induces generation of AMPs in a synergistic way.

SUMMARY OF THE INVENTION

In a first aspect, the present invention relates to a topical composition comprising from 0.001 to 10% by weight a compound of formula I,

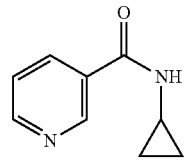

Formula I

In a second aspect, the present invention relates to a method of disinfecting a surface comprising the step of applying on to the surface a composition of the first aspect.

In a third aspect, the present invention relates to use of a composition of the first aspect for obtaining an antimicrobial benefit.

In a fourth aspect, the present invention relates to use of a composition of the first aspect for inducing generation of AMPs when applied on to an external surface of the human body.

Any feature of one aspect of the present invention may be utilized in any other aspect of the invention. The word "comprising" is intended to mean "including" but not necessarily "consisting of" or "composed of." In other words, the listed steps or options need not be exhaustive. Except in the operating and comparative examples, or where otherwise explicitly indicated, all numbers in this description indicating amounts of material or conditions of reaction, physical properties of materials and/or use are to be understood as modified by the word "about". Numerical ranges expressed in the format "from x to y" are understood to include x and y. When for a specific feature multiple preferred ranges are described in the format "from x to y", it is understood that all ranges combining the different endpoints are also contemplated.

DETAILED DESCRIPTION OF THE INVENTION

In a first aspect, the present invention relates to a topical composition comprising a compound of formula I, i.e. N-cyclopropyl nicotinamide, that has the following structure:

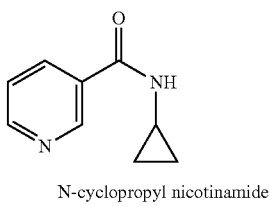

Formula I

N-cyclopropyl nicotinamide

The composition comprises from 0.001 to 10%, preferably from 0.005 to 8%, more preferably from 0.01 to 6%, even more preferably from 0.05 to 5%, further more preferably from 0.1 to 4%, still more preferably from 0.5 to 3% and yet more preferably from 1 to 1.5% by weight of the compound of formula I.

The composition preferably further comprises at least one ingredient selected from niacinamide, picolinamide and iso-nicotinamide. More preferably, the ingredient selected is niacinamide.

Niacinamide, also known as nicotinamide, is an amide form of nicotinic acid. It is a vitamin found in food. It is also used as a dietary supplement. Niacinamide, has the following chemical structure:

Niacinamide

Picolinamide and iso-niacinamide are the isomers of niacinamide and having the following structures:

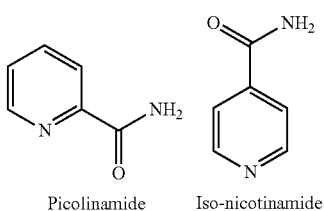

Picolinamide     Iso-nicotinamide

When present, the composition comprises from 0.001 to 10%, preferably from 0.005 to 8%, more preferably from 0.01 to 6%, even more preferably from 0.05 to 5%, further more preferably from 0.1 wt to 4%, still more preferably from 0.5 to 3% and yet more preferably from 1 to 1.5%, of niacinamide or picolinamide or iso-nicotinamide.

If more than one of these three actives are present at the same time, the total amount of these compounds that may be comprised in the composition ranges from 0.001 to 10%, preferably from 0.005 to 8%, more preferably from 0.01 to 6%, even more preferably from 0.05 to 5%, further more preferably from 0.1 wt to 4%, still more preferably from 0.5 to 3% and yet more preferably from 1 to 1.5% by weight.

The composition preferably further comprises a cosmetically acceptable base. The cosmetically acceptable base is preferably in the form of a cream, lotion, gel or emulsion.

The compositions may be prepared using different cosmetically acceptable emulsifying or non-emulsifying base.

A highly suitable base is a cream. Vanishing creams are especially preferred. Vanishing cream bases generally comprise a mixture of fatty acid and soap. Vanishing cream base gives a highly appreciated matty feel to the skin. C12 to C20 fatty acids are especially preferred in vanishing cream bases, further more preferred being C14 to C18 fatty acids. Most preferably, the fatty acids are stearic acid or palmitic acid or mixtures thereof. The fatty acid is often hystric acid which is substantially (generally from 90 to 95% by weight) a mixture of 45% stearic and 55% palmitic acid. Thus, inclusion of hystric acid and its soap to prepare compositions of the invention is within the scope of the present invention. The fatty acid in the composition is preferably present in an amount from 5 to 20%, more preferably from 6 to 19% and even more preferably from 7 to 17% by weight of the composition. Soaps in the vanishing cream base include alkali metal salt of fatty acids, like sodium or potassium salts, most preferred being potassium stearate. The soap in the vanishing cream base is generally present in an amount in the range from 0.1 to 10%, more preferably from 0.1 to 3% by weight of the composition. Generally, the vanishing cream base topical compositions are prepared by taking a desired amount of total fatty matter and mixing with potassium hydroxide in desired amounts. The soap is usually formed in-situ during the mixing.

An especially suitable cosmetically acceptable base is one which comprises a water-in-oil emulsion comprising silicone oils as the continuous phase. The water-in-oil emulsions preferably comprise a cross-linked silicone elastomer blend.

Inclusion of silicone elastomer blend in a water-in-oil emulsion may be used as the cosmetically acceptable base for preparing the compositions of the present invention. While silicone fluids may be used, silicone elastomers which are cross-linked, are especially preferred. In contrast to silicone fluid polymers, the physical properties of elastomers are typically dependent on the number of cross-linkages, rather than molecular weight. The ability of silicone elastomers to swell makes them ideal thickeners for oil phases. The elastomers have a very smooth and soft feel when applied to skin or hair. They can also be used as delivery agents for fragrances, vitamins and other additives in cosmetic compositions. Suitable silicone elastomer blends or gels which are commercially available and suitable for inclusion in the composition of the invention and found to provide the enhanced stability are: Dow Corning® EL-8051 IN Silicone Organic Elastomer Blend [INCI Name: Isodecyl Neopentanoate (and) Dimethicone/Bis Isobutyl PPG-20 Crosspolymer], EL-8050 [INCI Name: Isododecane (and) Dimethicone/Bis-Isobutyl PPG 20 Crosspolymer], DC9040, DC9041, DC9045 (Dimethicone crosspolymer), DC9506, DC9509 (Dimethicone vinyl dimethicone crosspolymer) and Shin-Etsu KSG-15, KSG-16, KSG-17 (Dimethicone vinyl dimethicone crosspolymer). It is further preferred that the composition comprises from 5 to 50% by weight silicone elastomer.

Water and/or alcohol may also be used a cosmetically acceptable base. Alcohol may be a mono or polyhydric alcohol. Monohydric alcohols often are short chain, by which is meant that they contain up to 6 carbons, and in practice is most often ethanol or sometimes iso-propanol. Polyhydric alcohols commonly comprise ethylene or propylene glycol, or a homologue can be employed such as diethylene glycol.

The cosmetically acceptable base is usually from 10 to 99.9%, preferably from 50 to 99% by weight of the composition.

Preferably, the composition further comprises skin lightening agents. Examples of skin lightening agents that may be used in the composition include, 12-hydroxystearic acid, aloe extract, ammonium lactate, arbutin, azelaic acid, kojic acid, butyl hydroxy anisole, butyl hydroxy toluene, citrate esters, 3 diphenyl propane derivatives, 2, 5 dihydroxybenzoic acid and its derivatives, ellagic acid, fennel extract, gluco pyranosyl-1-ascorbate, gluconic acid, glycolic acid, green tea extract, hydroquinone, 4 hydroxyanisole and its derivatives, 4-hydroxy benzoic acid derivatives, hydroxycaprylic acid, lemon extract, linoleic acid, magnesium ascorbyl phosphate, mulberry root extract, 2,4 resorcinol derivatives, 3,5 resorcinol derivatives, salicylic acid, vitamins like vitamin B6, vitamin B12, vitamin C, vitamin A, a dicarboxylic acid, resorcinol derivatives, hydroxycarboxylic acid like lactic acid and their salts e.g. sodium lactate and mixtures thereof.

Preferably, the composition further comprises one or more sunscreens. Any sunscreen that can be suitably used with the base may be added. Both, UVA and UVB sunscreens may preferably be added.

The composition of the invention may preferably comprises a UV-A sunscreen which is a dibenzoylmethane or its derivatives. Preferred dibenzoylmethane derivatives are selected from 4-tert-butyl-4'-methoxydibenzoylmethane, 2-methyldibenzoylmethane, 4-methyl-dibenzoylmethane, 4-isopropyldibenzoyl-methane, 4-tert-butyldibenzoylmethane, 2,4-dimethyldibenzoylmethane, 2,5-dimethyldibenzoylmethane, 4,4'-diisopropyl-dibenzoylmethane, 2-methyl-5-isopropyl-4'-methoxydibenzoylmethane, 2-methyl-5-tert-butyl-4'-methoxy-dibenzoyl methane, 2,4-dimethyl-4'-methoxy dibenzoylmethane or 2,6-dimethyl-4-tert-butyl-4'-methoxy-dibenzoylmethane. The most preferred dibenzoylmethane derivative is 4-tert-butyl-4'-methoxydibenzoylmethane. The composition of the invention preferably comprises from 0.1 to 10%, more preferably from 0.2 to 5%, further more preferably from 0.4 to 3%, by weight dibenzoylmethane or a derivative thereof based on total weight of the composition and including all ranges subsumed therein.

The composition may also preferably comprises a UV-B organic sunscreen selected from the class of cinnamic acid, salicylic acid, diphenyl acrylic acid and derivatives thereof. Illustrative non-limiting example of UV-B sunscreens which are commercially available and useful for inclusion in the composition of the invention are Octisalate™, Homosalate™, NeoHelipan™, Octocrylene™, Oxybenzone™ or Parsol MCX™. The UV-B sunscreen is most preferably 2-ethyl-hexyl-4-methoxy cinnamate which is commercially available as Parsol MCX™. The UV-B organic sunscreen is preferably included in the composition from 0.1 to 10%, more preferably from 0.1 to 7% by weight of the composition. It has been observed that presence of an organic UV-B sunscreen like 2-ethyl-hexyl-4-methoxy cinnamate causes further rapid degradation of the UV-A dibenzoylmethane sunscreen in the presence of UV radiation. The presence of the rosmarinic acid ester compound is found to be very efficacious in stabilizing the composition even when UV-B sunscreens are present.

Useful inorganic sun-blocks are also preferably used in the present invention. These include, for example, zinc oxide, iron oxide, silica, such as fumed silica, and titanium dioxide.

The composition may further comprise preservatives to protect against the growth of potentially harmful microorganisms. Suitable traditional preservatives for compositions of this invention are alkyl esters of para-hydroxybenzoic acid. Other preservatives which have more recently come into use include hydantoin derivatives, propionate salts, and a variety of quaternary ammonium compounds. Particularly preferred preservatives are phenoxyethanol, methyl paraben, propyl paraben, imidazolidinyl urea, sodium dehydroacetate, benzyl alcohol, alkane diols most preferably 1,2-octane diol and phenoxyethanol. The preservatives should be selected having regard for the use of the composition and possible incompatibility between the preservatives and other ingredients. Preservatives are preferably employed in amounts from 0.01% to 2% by weight of the composition.

A variety of other optional materials may be formulated into the compositions. These may include: antimicrobials such as 2-hydroxy-4,2',4'-trichlorodiphenylether (triclosan), 2,6-dimethyl-4-hydroxychlorobenzene, and 3,4,4'-trichlorocarbanilide, scrub and exfoliating particles such as polyethylene and silica or alumina; cooling agents such as menthol; skin calming agents such as aloe vera; and colorants.

In addition, the compositions may further comprise from 0 to 10% by weight of opacifiers and pearlizers such as ethylene glycol distearate, titanium dioxide or Lytron® 621 (Styrene/Acrylate copolymer); all of which are useful in enhancing the appearance or properties of the product.

Diluents other than water that may be used in the composition includes liquid or solid emollients, solvents, humectants, thickeners and powders. Examples of each of these types of vehicle, which can be used singly or as mixtures of one or more vehicles, are as follows:

Preferably, the composition comprises emollients. Examples of emollients that may be present include stearyl alcohol, glyceryl monoricinoleate, mink oil, cetyl alcohol, isopropyl isostearate, stearic acid, isobutyl palmitate, isocetyl stearate, oleyl alcohol, isopropyl laurate, hexyl laurate, decyl oleate, octadecan-2-ol, isocetyl alcohol, eicosanyl alcohol, behenyl alcohol, cetyl palmitate, silicone oils such as dimethylpolysiloxane, di-n-butyl sebacate, isopropyl myristate, isopropyl palmitate, isopropyl stearate, butyl stearate, polyethylene glycol, triethylene glycol, lanolin, cocoa butter, corn oil, cotton seed oil, olive oil, palm kernel oil, rape seed oil, safflower seed oil, evening primrose oil, soybean oil, sunflower oil, avocado oil, sesame seed oil, coconut oil, *arachis* oil, castor oil, acetylated lanolin alcohols, petroleum jelly, mineral oil, butyl myristate, isostearic acid, palmitic acid, isopropyl linoleate, lauryl lactate, myristyl lactate, decyl oleate, myristyl myristate.

Preferably, the composition comprises solvents such as ethyl alcohol, isopropanol, acetone, ethylene glycol monoethyl ether, diethylene glycol monobutyl ether, diethylene glycol monoethyl ether and mixtures thereof.

Advantageously, the composition may preferably comprise ingredients like bactericides, vitamins, anti-acne actives, anti-wrinkle, anti-skin atrophy and skin repair actives, skin barrier repair actives, non-steroidal cosmetic soothing actives, artificial tanning agents and accelerators, sebum stimulators, sebum inhibitors, anti-oxidants, protease inhibitors, skin tightening agents, anti-itch ingredients, hair growth inhibitors, 5-alpha reductase inhibitors, desquamating enzyme enhancers, anti-glycation agents and mixtures thereof.

The composition may preferably comprise powders like e.g. chalk, talc, fullers earth, kaolin, starch, gums, colloidal silica sodium polyacrylate, tetra alkyl and/or trialkyl aryl ammonium smectites, chemically modified magnesium aluminium silicate, organically modified montmorillonite clay, hydrated aluminium silicate, fumed silica, carboxyvinyl polymer, sodium carboxymethyl cellulose, ethylene glycol monostearate and mixtures thereof.

The compositions of the present invention can comprise a wide range of other optional components. The CTFA Personal care Ingredient Handbook, Second Edition, 1992, which is incorporated by reference herein in its entirety, describes a wide variety of non-limiting personal care and pharmaceutical ingredients commonly used in the skin care industry, which are suitable for use in the compositions of the present invention. Examples include: antioxidants, binders, biological additives, buffering agents, colorants, thickeners, polymers, astringents, fragrance, humectants, opacifying agents, conditioners, pH adjusters, natural extracts, essential oils, skin sensates, skin soothing agents, and skin healing agents.

The composition may also comprise one or more of the following ingredients e.g. benzethonium chloride (BEC), benzalkonium chloride (BKC), chloroxylenol, zinc pyrithione (ZPT), creatine and creatinine.

The composition is preferably in the form of a wash-off or a leave-on composition, preferably a leave-on composition.

Wash-off composition preferably means composition which is intended/required to be removed from the body by washing with solvent preferably water after the application of the composition like e.g. hand wash composition and face wash composition.

Leave-on composition preferably means composition which is not required to be removed from the human body after the application of the composition like e.g. skin cream, body lotion, hand sanitizer and deodorants.

When the composition is in the form of a leave-on composition, the composition may be in the form of a deodorant, a hand sanitizer, a lotion, a cream and a body spray.

The composition of the invention may preferably comprise a conventional deodorant base as the cosmetically acceptable carrier. By a deodorant is meant a product in the stick, roll-on, or propellant medium which is used for personal deodorant benefit e.g. application in the under-arm area which may or may not contain anti-perspirant actives.

Deodorant compositions can generally be in the form of firm solids, soft solids, gels, creams, and liquids and are dispensed using applicators appropriate to the physical characteristics of the composition. Deodorant compositions which are delivered through roll-ons generally comprise a liquid carrier. Such liquid carrier can be hydrophobic or comprise a mixture of both hydrophilic and hydrophobic liquids. They may be in the form of an emulsion or a microemulsion. The liquid carrier or mixture of carriers often constitutes from 30 to 95% and in many instances from 40 to 80% by weight of the composition. Hydrophobic liquid carriers commonly can comprise one or more materials selected within the chemical classes of siloxanes, hydrocarbons, branched aliphatic alcohols, esters and ethers that have a melting point not higher than 25° C. and a boiling point of at least 100° C. Hydrophilic carrier liquids that can be employed in compositions herein commonly comprise water and/or a mono or polyhydric alcohol or water-miscible homologue. Monohydric alcohols often are short chain, by which is meant that they contain up to 6 carbons, and in practice is most often ethanol or sometimes iso-propanol. Polyhydric alcohols commonly comprise ethylene or propylene glycol, or a homologue can be employed such as diethylene glycol. Other than this suitable other vehicle and component used for deodorant composition can be added.

When the composition is in the form of a hand sanitizer the cosmetically acceptable base may comprises of alcohol and water. The most preferred alcohols are ethyl alcohol and isopropyl alcohol. Even a mixture of two or more alcohol can preferably be used in the hand sanitizer composition. The amount of alcohol preferably is in the range from 50 to 95%, more preferably 60 to 80% and most preferably 65 to 80% by weight of the hand sanitizer composition.

The present invention also provides a method of cleaning or disinfecting a surface comprising the steps of applying the composition described in the first aspect on to said surface in case of a leave-on composition. This method optionally comprises an additional step of at least partially removing the composition from the surface if it is in the form of a wash-off composition. Preferably, the step of at least partially removing the composition is carried out in less than 5 minutes after the step of applying the composition on to the substrate. Preferably, the method is non-therapeutic.

The present invention further provides an use of the composition of the present invention for obtaining an antimicrobial benefit. An antimicrobial benefit preferably means the capability of killing or at least cause substantial reduction of the common disease causing microbes. The common disease causing gram-positive organisms includes *Staphylococcus, Streptococcus* and *Enterococcus* spp. Some of common disease causing gram-negative organisms includes *Escherichia coli, Salmonella, Klebsiella* and *Shigella. Escherichia coli* and *Salmonella* can cause severe gastrointestinal illnesses. The composition of the present invention provides improved antimicrobial benefits.

The present invention also provides an use of the composition of the present invention for inducing secretion of AMPs when applied on an external surface of the human body. The external surface includes skin, scalp or oral cavity.

Without wishing to be bound by theory it is believed that the compound of formula I activates keratinocytes, which are the major cells in the skin epidermis to provide the benefits of the present invention viz. inducing secretion of AMPs. This causes to boost protection shield against germs. The composition comprising the compound of formula I therefore provides protection to the body against infections by boosting the body's own defense. In other words, the compound of formula I primes the body surface for germ protection. The advantage of this is such that it provides long-lasting protection e.g. up to 24 hours of protection against germs.

The use of the composition of the present invention may preferably for hand hygiene.

The intended use of the composition may be for therapeutic or non-therapeutic purpose. However, the preferred intended use of the composition of the present invention is non-therapeutic and/or cosmetic.

The present invention also provides use of a combination of the compound of formula I and a compound selected from niacinamide, picolinamide, iso-nicotinamide and mixtures thereof, for inducing the secretion of anti-microbial peptides. Preferably, the compound selected is niacinamide. It has been surprisingly found that the compound of formula I and niacinamide when used in select concentrations induce generation of AMPs in a synergistic way. Thus, the invention preferably provides use of a combination of the compound of formula I and a compound selected from niacinamide, picolinamide, iso-nicotinamide and mixtures thereof, in a composition comprising a cosmetically acceptable base for synergistically inducing generation of AMPs. The preferences with regards to the composition of the present invention apply equally to the use of combination of the compound of formula I and at least one compound selected from niacinamide, picolinamide and iso-nicotinamide, according to the invention.

The present invention now will be demonstrated by way of following non-limiting examples.

EXAMPLES

Example 1: Preparation of Compound of Formula I: N-Cyclopropyl Nicotinamide

Materials:

Nicotinic acid (sigma catalog no C115002), Propylphosphonic anhydride (T3P; Aldrich, Catalog no 87801), Dichloromethane anhydrous (DCM; Sigma, catalog no 270997), triethanolamine, Ethylacetate, Methanol, Sodium sulphate anhydrous ( ).

Experimental Procedure:

To a stirred solution of Nicotinic acid (1 g, 8.12 mmol, 1 equiv) in anhydrous DCM (10 vol) Propylphosphonic anhydride (T3P) (3.87 g, 50% solution in EtOAc, 12.18 mmol, 1.5 equiv), TEA (2.46 g, 24.3 mmol, 3 equiv) and Cyclopentylamine (0.76 g, 8.93 mmol, 1.1 equiv) at 0° C. under inert atmosphere. The reaction mixture was then allowed to stir at about 25° C. for about 12 hours. After completion of the reaction as monitored by Thin Layer Chromatography (TLC), reaction mass was partitioned between DCM and water. Layers were separated and aqueous layer was extracted again in 10% MeOH/DCM. The combined extract was washed with water, brine solution and dried ($Na_2SO_4$). Solvent was evaporated to dryness; crude product was then purified.

In-Vitro Experiment that Demonstrate Generation of Psoriasin; an Antimicrobial Peptide, by Human Keratinocytes after Treatment with the Compound of Formula I in Presence or Absence of Niacinamide:

The experiment was done using the following protocol:

Step 1: Human neonatal primary skin keratinocyte (NHEK) cells was obtained from Lonza®. The experiment was done with the above-mentioned cells with passage between 3 and 4. The cells were seeded (35,000 cells/well) in 24 well plate with keratinocyte growth media (KGM) obtained from Invitrogen®. The plate was then incubated at 37±2° C. in a $CO_2$ incubator for 48 hours.

Step 2: After 48 hours of incubation, cell differentiation was induced by replacing media with fresh KGM supplemented with 2 mM calcium chloride solution. This was then followed by incubation at 37±2° C. in a $CO_2$ incubator for 48 hours.

Step 3: After that, the cells were treated with niacinamide and the compound of formula I, i.e. N-cyclopropyl nicotinamide, in varying concentration as outlined in table 1 below with keratinocyte growth media supplemented with 2 mM calcium chloride solution.

TABLE 1

| Example No. | Niacinamide (µg/mL) | N-cyclopropyl Nicotinamide (µg/mL) |
|---|---|---|
| A | – | – |
| B | 100 | – |
| C | 250 | – |
| D | 500 | – |
| 1 | – | 100 |
| 2 | – | 250 |
| 3 | – | 500 |
| 4 | 100 | 500 |
| 5 | 500 | 500 |

Step 4: After the above treatment, cells were again incubated at 37±2° C. in a $CO_2$ incubator for 72 hours.

Step 5: After 72 hours of incubation, cell culture supernatant from each well was collected in a sterile tube. The samples were then stored at −80° C. until used for testing psoriasin secretion by standard ELISA technique using psoriasin ELISA kit obtained from Circulx® (No: CY-8073). In the current experiment, psoriasin was used as a marker for AMP.

Step 6: The ELISA method was performed by using 100 µL of cell culture supernatant from each sample.

The data is expressed in terms of fold change over control (no treatment: Example A). The fold change in psoriasin levels in case of control (example A) is taken to be equal to 1 fold. Any fold change in psoriasin obtained due to treatments outlined in all the other examples was over and above the 1 fold change obtained from the control. For example, example B shows fold change to be 1.26 fold which means, it is 0.26 fold over and above 1 fold that was obtained from the control. Likewise, example 5 shows fold change to be 2.75 which means it is 1.75 fold over and above 1 fold that was obtained from the control.

The results are summarized below in table 2 below:

TABLE 2

| Concentration of actives (Niacinamide and/or compound of formula 1) | Example No. | Fold change |
|---|---|---|
| — | A | 1.00 |
| 100 (µg/mL) | B | 1.26 |
|  | 1 | 1.61 |
| 250 (µg/mL) | C | 1.50 |
|  | 2 | 1.88 |
| 500 (µg/mL) | D | 1.44 |
|  | 3 | 2.16 |
| 100 (µg/mL) Niacinamide + 500 (µg/mL) compound of formula1 | 4 | 2.69 |
| 500 (µg/mL) Niacinamide + 500 (µg/mL) compound of formula1 | 5 | 2.75 |

From the table above, it is evident that the compositions comprising the compound of formula I alone, i.e. examples 1, 2 and 3 provides much better fold change in psoriasin generation as compared to the control (Example A). At the same time it is also clear that the compound of formula 1 is better and provides higher fold change in psoriasin generation at the same concentration when compared with niacinamide e.g. the psoriasin generation for Example 1 is higher than Example B. The observation is also holds true for Example 2 when compared with Example C and Example 3 when compared with Example 3.

It is also evident that when treatments as in example B (100 µg/mL niacinamide) and example 3 (500 µg/mL N-cyclopropyl nicotinamide) were combined as shown in example 4, a synergistic fold change in psoriasin was obtained. The synergistic effect is also observed for example 5 that is a combination of treatments in examples D (500 µg/mL niacinamide) and 3 (500 µg/mL N-cyclopropyl nicotinamide).

In conclusion, N-cyclopropyl nicotinamide, i.e. the compound of formula I, provides improved generation of AMPs as compared to control (no treatment) and compared to generation of AMPs by niacinamide. Lastly, the compound of formula I, when combined with niacinamide in select concentrations, a synergistic generation of AMPs was obtained. Thus, the composition provides improved antimicrobial benefit through improved generation of AMPs.

The invention claimed is:

1. A topical composition comprising from 0.001 to 10% by weight a compound of formula I,

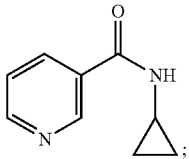

Formula I further comprising from 0.001 to 10% by weight of at least one ingredient selected from niacinamide, picolinamide and iso-nicotinamide.

2. The topical composition of claim 1, wherein the ingredient is niacinamide.

3. The topical composition of claim 1, further comprising a cosmetically accepted base.

4. The topical composition of claim 1, wherein the composition is in the form of a wash-off composition.

5. The topical composition of claim 1, wherein the composition is in the form of a leave-on composition.

6. The topical composition of claim 1, wherein said leave-on composition includes lotion, cream, deodorants, hand sanitizer and body spray.

7. The topical composition of claim 1, wherein the topical composition is configured for obtaining an antimicrobial benefit.

8. The topical composition of claim 7, wherein the antimicrobial benefit includes killing or reducing disease causing microbes.

9. The topical composition of claim 1, wherein the topical composition is configured to induce secretion of antimicrobial peptides when applied on an external surface of a human body.

10. The topical composition of claim 1, wherein the topical composition provides 24-hour protection against germs.

11. A method of disinfecting a surface comprising the step of applying on to the surface a composition as claimed in claim 1.

12. The method of claim 11, wherein the composition is in the form of a wash-off composition and wherein the method comprises an additional step of at least partially removing the composition.

13. The method of claim 12, wherein the step of at least partially removing the composition is carried out in less than 5 minutes after the step of applying the composition on the substrate.

14. A method for obtaining an antimicrobial benefit by using the topical composition of claim 1.

15. A method for inducing secretion of anti-microbial peptides (AMPs) when applied on an external surface of the human body by using the topical composition of claim 1.

16. The method of claim 14, comprising 0.001 to 10% of compound of formula 1,

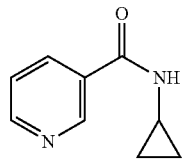

Formula I for the antimicrobial benefit.

* * * * *